United States Patent
Fehn et al.

(10) Patent No.: US 6,359,098 B1
(45) Date of Patent: Mar. 19, 2002

(54) CURABLE ORGANOPOLYSILOXANE MATERIALS

(75) Inventors: Armin Fehn, Emmerting; Frank Achenbach, Simbach, both of (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 09/638,101

(22) Filed: Aug. 11, 2000

(30) Foreign Application Priority Data

Aug. 13, 1999 (DE) .......................................... 199 38 338

(51) Int. Cl.⁷ .............................................. C08G 77/08
(52) U.S. Cl. ........................ 528/15; 502/152; 502/158; 502/262
(58) Field of Search ............................. 528/15; 502/152, 502/158, 262

(56) References Cited

U.S. PATENT DOCUMENTS

| | | |
|---|---|---|
| 4,329,275 A | 5/1982 | Hatanaka et al. |
| 5,328,974 A | 7/1994 | McAfee et al. |
| 6,187,890 B1 * | 2/2001 | Fehn et al. .................... 528/15 |

FOREIGN PATENT DOCUMENTS

| | | |
|---|---|---|
| DE | 36 35 236 A1 | 5/1987 |
| DE | 44 20 884 A1 | 12/1995 |
| DE | 44 29 411 A1 | 2/1996 |
| EP | 0 173 512 A2 | 3/1986 |
| EP | 0 363 006 A2 | 11/1990 |
| EP | 0 490 523 A2 | 6/1992 |
| EP | 0 583 159 A2 | 2/1994 |
| EP | 0 627 467 B1 | 12/1994 |
| EP | 0 982 370 A1 | 3/2000 |
| EP | 0 994 159 A1 | 4/2000 |

OTHER PUBLICATIONS

English Derwent Abstract Corresponding To EP 0 982 370.
English Derwent Abstract Corresponding To EP 0 994 159.
Derwent Abstract Corresponding To DE 3, 635 236 (AN 1987–072445).
Organometallics (1992) 11 2873–2883.
J. Chem. Soc., Dalton Trans. (1986), 1987–92.
J. Chem. Soc., (C) 1967, 1364–1366.
R.J. Cross, M. F. Davidson, J. Chem. Soc. Dalton Trans. 1986, 1087–1992.
S.D. Perera, B.L. Shaw, M. Thornton–Pett, J. Chem. Soc. Dalton Trans. 1993, 3653–3659.
Derwent Abstract Corresponding To DE 4,429,411 (AN 1996–117700).
Derwent Abstract Corresponding To DE 4,420,884 (AN 1996–040863).

\* cited by examiner

*Primary Examiner*—Margaret Moore
*Attorney, Agent, or Firm*—Brooks & Kushman P.C.

(57) ABSTRACT

Curable addition crosslinkable organopolysiloxane materials employing a platinum catalyst selected from the group consisting of compounds of the formula

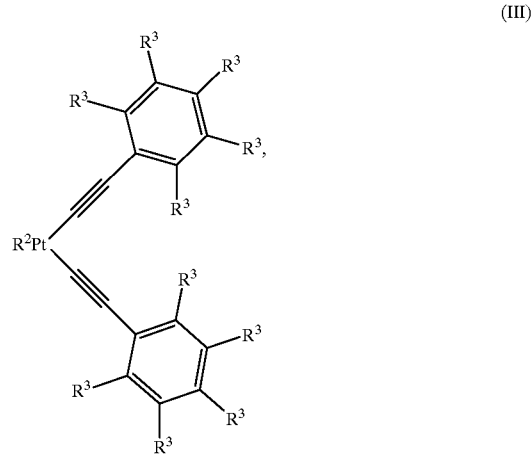

(III)

and/or oligomeric or polymeric compounds which are composed of structural units of the general formula

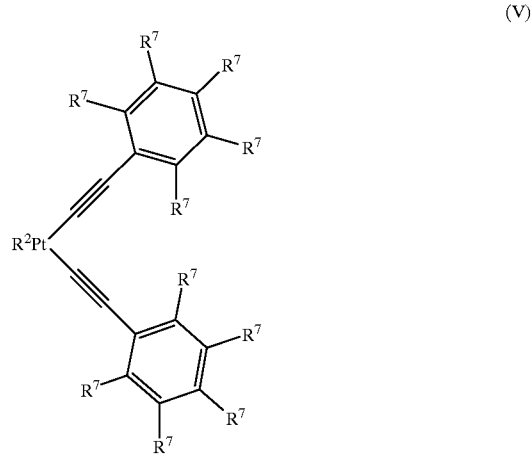

(V)

and optionally structural units of the general formula $$R^9{}_r SiO_{(4-r)/2}$$

in which $R^2$, $R^3$, $R^4$, $R^6$, $R^7$, $R^8$, $R^9$, r, s and t have the meanings stated in claim 1, may be prepared as one-component formulations having prolonged shelf life, or as two-component formulations having prolonged pot life, while maintaining desirable chemical and physical properties.

17 Claims, No Drawings

CURABLE ORGANOPOLYSILOXANE MATERIALS

TECHNICAL FIELD

The present invention relates to silicone materials crosslinkable by addition of Si-bonded hydrogen at an aliphatic carbon-carbon multiple bond, processes for their preparation, platinum catalysts used for this purpose and the use of the crosslinkable materials.

BACKGROUND ART

Addition-crosslinking silicone materials crosslink by reaction of aliphatically unsaturated groups with Si-bonded hydrogen (hydrosilylation) in the presence of a catalyst, typically a platinum compound. Owing to the fact that the crosslinking reaction starts as soon as the essential constituents are simultaneously present, addition-crosslinking silicone materials have thus far been prepared almost exclusively as two-component formulations, the composition of the individual components being such that all three essential constituents are simultaneously present only after the individual components have been mixed together. Usually, one of the components contains the polyorganosiloxane having alkenyl functional groups and the platinum catalyst, and the other component contains the crosslinking agent having SiH functional groups, if necessary, in combination with further polyorganosiloxane having alkenyl functional groups. After mixing of the individual components, complete curing to give the silicone elastomer can be effected at room temperature, but is usually carried out at elevated temperature.

The use of two-component addition-crosslinkable silicone materials is associated with numerous disadvantages, such as, for example, logistics, the high risk of contamination by traces of platinum, and the necessity for an additional mixing step. Although a ready-to-use material is obtained after mixing of the components, it has only a limited pot life at room temperature. This necessitates, on the one hand, processing quickly following mixing, and, on the other hand, frequent cleaning of the storage container, metering units, processing machines, etc., since the material remaining, for example, through back-mixing or adhesion to the container walls, ultimately gels.

Because of these disadvantages, there have been many attempts to provide addition-crosslinking silicone materials as a one-component formulation (1C system). Since in the case of a 1C system all constituents required for the crosslinking are present together, the problem of suppressing premature crosslinking, which usually also takes place at room temperature, must be addressed. Possibilities for specifically controlling (increasing) the pot life of an addition-crosslinking material are sufficiently well known, for example through the use of inhibitors which are capable of considerably reducing the activity of the platinum catalyst at room temperature, such as, phosphorus compounds in combination with peroxides according to U.S. Pat. No. 4,329,275, or azodicarbonyl compounds according to EP-A-490 523. Although the pot life per se can be increased as desired through the type and content of such inhibitors, a disadvantageous effect on the crosslinking behavior is also inevitably associated with increasing pot life, particularly when the pot life is extended to several months by high inhibitor contents. Higher initiation temperatures and low crosslinking rate as well as undercrosslinking are the result in such cases.

A further possibility fundamentally differing from the use of inhibitors consists of encapsulating the platinum catalyst in a finely divided material which does not release the platinum until an elevated temperature has been reached. This can be effected, for example, by microencapsulation of the platinum catalyst with a thermoplastic silicone resin or an organic thermoplastic, as described, for example, in EP-A-363 006, which, however, is relatively expensive.

A third possibility consists in selecting, as the catalyst, specific platinum complexes whose activity is such that the hydrosilylation reaction takes place sufficiently rapidly at elevated temperature but to such a small extent at room temperature that pot lives of several months are achieved. Such addition-crosslinking materials containing platinum complexes were described, for example, in EP-A-583 159 and DE -A-36 35 236. Although the materials described have substantially improved pot lives with, in some cases, sufficiently high crosslinking rates, there is still a need for improving the pot life and crosslinking rate of addition-crosslinking materials formulated as a single component through use of more efficient platinum catalysts, without having to accept the abovementioned disadvantages.

DISCLOSURE OF INVENTION

The present invention provides addition-crosslinkable compositions containing aliphatically unsaturated compounds and Si-H-functional organopolysiloxanes together with unique platinum complexes which allow for extended shelf life as one-component addition-curable organopolysiloxanes, and extended pot life for two-component addition-curable organopolysiloxanes, without compromising crosslinking rates or levels.

BEST MODE FOR CARRYING OUT THE INVENTION

The present invention thus relates to curable organopolysiloxane materials containing (A) compounds which have radicals having aliphatic carbon-carbon multiple bonds, (B) organopolysiloxanes having Si-bonded hydrogen atoms or, instead of (A) and (B) or in addition thereto, (C) organopolysiloxanes which have SiC-bonded radicals having aliphatic carbon-carbon multiple bonds and Si-bonded hydrogen atoms, and (D) a platinum catalyst selected from the group consisting of compounds of the formula

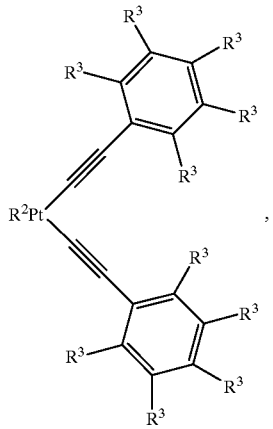

(II)

and/or oligomeric or polymeric compounds which are composed of structural units of the general formula

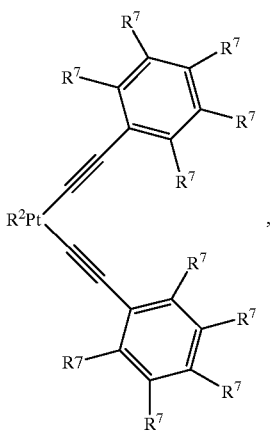

(V)

and optionally chemically bonded structural units of the general formula $$R^9_r SiO_{(4-r)/2} \qquad (VI)$$

in which $R^2$ denotes an optionally substituted diene which is linked by at least one π-bond to platinum and represents a straight or a branched chain having 4 to 18 carbon atoms or a cyclic ring having 6 to 28 carbon atoms, $R^3$ is identical or different and denotes a hydrogen atom, a halogen atom, —SiR$^4_3$, —OR$^6$ or monovalent, optionally substituted hydrocarbon radicals having 1 to 24 carbon atoms, with the proviso that, in the compounds of the formula (III), at least one radical $R^3$ denotes —SiR$^4_3$, $R^4$ is identical or different and denotes hydrogen, a halogen atom, —OR$^6$ or monovalent, optionally substituted hydrocarbon radicals having 1 to 24 carbon atoms, $R^6$ is identical or different and is a hydrogen atom, —SiR$^4_3$ or a monovalent, optionally substituted hydrocarbon radical having 1 to 20 carbon atoms, $R^7$ is identical or different and denotes a hydrogen atom, a halogen atom, —SiR$^4_3$, —SiR$^4_{(3-t)}[R^8SiR^9_sO_{(3-s)/2}]_t$, —OR$^6$, or monovalent optionally substituted hydrocarbon radicals having 1 to 24 carbon atoms, with the proviso that, in formula (V), at least one radical $R^7$ denotes —SiR$^4_{(3-t)}[R^8SiR^9_sO_{(3-s)/2}]_t$, $R^8$ is identical or different and denotes oxygen or divalent, optionally substituted hydrocarbon radicals having 1 to 24 carbon atoms, which may be bonded to the silicon via an oxygen atom, $R^9$ is identical or different and denotes hydrogen or an organic radical, r is 0, 1, 2 or 3, s is 0, 1, 2 or 3 and t is 1, 2 or 3.

Within the scope of the present invention, the term organopolysiloxane is intended to include polymeric, oligomeric and dimeric siloxanes.

If $R^2$ is a substituted diene or the radicals $R^3$, $R^4$, $R^5$, $R^6$, $R^7$ and $R^8$ are substituted hydrocarbon radicals, preferred substituents are halogen atoms such as F, Cl, Br and I, cyano radicals, —NR$^6_2$, heteroatoms such as O, S, N and P, and groups —OR$^6$, in which $R^6$ has the abovementioned meaning.

The compositions according to the invention may be one-component organopolysiloxane materials as well as two-component organopolysiloxane materials. In the latter case, the two components of the materials according to the invention may contain all constituents in any desired combination, in general with the proviso that one component does not simultaneously contain siloxanes having an aliphatic multiple bond, siloxanes having Si-bonded hydrogen and catalysts, i.e. essentially not simultaneously the constituents (A), (B) and (D) or (C) and (D). Preferably, the compositions according to the invention are one-component materials.

The compounds (A) and (B) or (C) used in the materials according to the invention are known to be chosen in such a way that crosslinking is possible. Thus, for example, on average, compound (A) has at least two aliphatically unsaturated radicals and siloxane (B) has at least three Si-bonded hydrogen atoms, or compound (A) has at least three aliphatically unsaturated radicals and siloxane (B) has at least two Si-bonded hydrogen atoms, or siloxane (C) which has aliphatically unsaturated radicals and Si-bonded hydrogen atoms in the abovementioned ratios is used instead of compounds (A) and (B).

The compound (A) used according to the invention may also be silicon-free organic compounds preferably having at least two aliphatically unsaturated groups, and organosilicon compounds having preferably at least two aliphatically unsaturated groups. Examples of organic compounds which can be used as component (A) in the materials according to the invention are 1,3,5-trivinylcyclohexane, 2,3-dimethyl-1,3-butadiene, 7-methyl-3-methylene-1,6-octadiene, 2-methyl-1,3-butadiene, 1,5-hexadiene, 1,7-octadiene, 4,7-methylene-4,7,8,9-tetrahydroindene, methylcyclopentadiene, 5-vinyl-2-norbornene, bicyclo[2.2.1]hepta-2,5-diene, 1,3-diisopropylbenzene, polybutadiene containing vinyl groups, 1,4-divinylcyclohexane, 1,3,5-triallylbenzene, 1,3,5-trivinylbenzene, 1,2,4-trivinylcyclohexane, 1,3,5-triisopropenylbenzene, 1,4-divinylbenzene, 3-methyl-1,5-heptadiene, 3-phenyl-1,5-hexadiene, 3-vinyl-1,5-hexadiene and 4,5-dimethyl-4,5-diethyl-1,7-octadiene, N,N'-methylenebis(acrylamide), 1,1,1-tris(hydroxymethyl)-propane triacrylate, 1,1,1-tris(hydroxymethyl)propane trimethacrylate, tripropylene glycol diacrylate, diallyl ether, diallylamine, diallyl carbonate, N,N'-diallylurea, triallylamine, tris(2-methylallyl)amine, 2,4,6-triallyloxy-1,3,5-triazine, triallyl-s-triazine-2,4,6(1H,3H,5H)trione, diallylmalonic esters, polyethylene glycol diacrylate, polyethylene glycol dimethacrylate and poly(propylene glycol) methacrylate. This list is illustrative, and not limiting.

However, the silicone materials according to the invention preferably contain, as constituent (A), an aliphatically unsaturated organosilicon compound, it being possible to use all aliphatically unsaturated organosilicon compounds used to date in addition-crosslinking materials including, for example, silicone block copolymers having urea segments, silicone block copolymers having amide segments and/or imide segments and/or ester-amide segments and/or polystyrene segments and/or silarylene segments and/or carborane segments and silicone graft copolymers having ether groups.

Linear or branched organopolysiloxanes comprising units of the formula $$R_a R^1_b SiO_{(4-a-b)/2} \qquad (I)$$

in which

R may be identical or different and denotes an organic radical free of aliphatic carbon-carbon multiple bonds, R¹ may be identical or different and denotes a monovalent, optionally substituted, SiC-bonded hydrocarbon radical having an aliphatic carbon-carbon multiple bond, a is 0, 1, 2 or 3 and b is 0, 1 or 2, with the proviso that the sum a+b is less than or equal to 3 and on average at least 2 radicals R¹, are present per molecule, are preferably used as organosilicon compounds (A) which have SiC-bonded radicals having aliphatic carbon-carbon multiple bonds.

Radicals R may be monovalent or polyvalent radicals, the polyvalent radicals, such as bivalent, trivalent and tetravalent radicals, thus linking together a plurality of silyloxy units of the formula (I), such as, two, three or four of said silyloxy units. R also may be a monovalent radical such as —F, —Cl, —Br, —OR⁶, —CN, —SCN, —NCO and SiC-bonded optionally substituted hydrocarbon radicals optionally interrupted by oxygen atoms or the group —C(O)—, and divalent radicals Si-bonded on both sides according to formula (I).

If radical R denotes SiC-bonded, substituted hydrocarbon radicals, preferred substituents are halogen atoms, phosphorus-containing radicals, cyano radicals, —OR⁶, —NR⁶—, NR⁶₂, —NR⁶—C(O)—NR⁶₂, —C(O)—NR⁶₂, —C(O)—R⁶, —C(O)OR⁶, —SO₂—Ph and —C₆F₅, in which R⁶ has the abovementioned meaning and Ph is a phenyl radical.

Examples of radicals R are alkyl radicals such as the methyl, ethyl, n-propyl, isopropyl, n-butyl, isobutyl, tert-butyl, n-pentyl, isopentyl, neopentyl and tert-pentyl radicals; hexyl radicals such as the n-hexyl radical; heptyl radicals such as the n-heptyl radical; octyl radicals such as the n-octyl radical and isooctyl radicals, for example the 2,2,4-trimethylpentyl radical; nonyl radicals such as the n-nonyl radical; decyl radicals such as the n-decyl radical; dodecyl radicals such as the n-dodecyl radical; and octadecyl radicals such as the n-octadecyl radical; cycloalkyl radicals such as cyclopentyl, cyclohexyl, cycloheptyl and methylcyclohexyl radicals; aryl radicals such as the phenyl, naphthyl, anthryl and phenanthryl radicals; alkaryl radicals such o-, m-, and p-tolyl radicals, xylyl radicals and ethylphenyl radicals; and aralkyl radicals such as the benzyl radical and the α- and β-phenylethyl radicals.

Examples of substituted radicals R are haloalkyl radicals, such as the 3,3,3-trifluoro-n-propyl radical, the 2,2,2,2',2',2'-hexafluoroisopropyl radical, the heptafluoroisopropyl radical, haloaryl radicals, such as the o-, and p-chlorophenyl. radical, —(CH₂)ₙ—N(R⁶)C(O)NR⁶₂, —(CH₂)ₙ—C(O) NR⁶₂, —(CH₂)ₙ—C(O)R⁶, —(CH₂)ₙ—C(O)OR⁶, —(CH₂)ₙ —C(O)NR⁶₂, —(CH₂)ₙ—C(O)—(CH₂)ₘ—C(O)CH₃, —(CH₂)ₙ—NR⁶—(CH₂)ₘ—NR⁶₂, —(CH₂)ₙ—O—CO— R⁶, —(CH₂)ₙ—O—(CH₂)ₘ—CH(OH)—CH₂OH, —(CH₂)ₙ—(OCH₂CH₂)ₘ—OR⁶, —(CH₂)ₙ—SO₂—Ph and —(CH₂)ₙ—O—C₆F₅, in which R⁶ has the meanings stated therefor above, n and m are identical or different integers between 0 and 10 and Ph designates the phenyl radical.

Examples of divalent radicals R Si-bonded on both sides according to Formula (I) are those which are derived from the monovalent examples stated above for radical R by providing an additional bond by substitution of a hydrogen atom. Examples of such radicals are —(CH₂)ₙ—, —CH(CH₃)—, —C(CH₃)₂—, —CH(CH₃)—CH₂—, —C₆H₄—, —CH(Ph)—CH₂—, —C(CF₃)₂—, —(CH₂)ₙ—C₆H₄—(CH₂)ₙ—, —(CH₂)ₙ—C₆H₄—C₆H₄—(CH₂)ₙ——(CH₂O)ₘ—, —(CH₂CH₂O)ₘ—, —(CH₂)ₙ—Oₓ—C₆H₄—SO₂—C₆H₄—Oₓ—(CH₂)ₙ—, in which x is 0 or 1, m and n have the abovementioned meaning and Ph is a phenyl radical.

Radical R is preferably a monovalent, SiC-bonded, optionally substituted hydrocarbon radical free of aliphatic carbon-carbon multiple bonds and having 1 to 18 carbon atoms, particularly preferably a monovalent, SiC-bonded hydrocarbon radical free of aliphatic carbon-carbon multiple bonds and having 1 to 6 carbon atoms, in particular the methyl or phenyl radical.

Radical R¹ may be one of any desired groups susceptible to addition reaction (hydrosilylation) with a compound having SiH functional groups. If R¹ is an SiC-bonded, substituted hydrocarbon radical, the preferred substituents are halogen atoms, cyano radicals and —OR⁶, in which R⁶ has the abovementioned meaning. Radical R¹ is preferably an alkenyl or alkynyl group having 2 to 16 carbon atoms, such as a vinyl, allyl, methallyl, 1-propenyl, 5-hexenyl, ethynyl, butadienyl, hexadienyl, cyclopentenyl, cyclopentadienyl, cyclohexenyl, vinylcyclohexylethyl, divinylcyclohexylethyl, norbornenyl, vinylphenyl, or styryl radical, the vinyl, allyl and hexenyl radicals being particularly preferred.

The molecular weight of constituent (A) may vary within wide limits, for example between 10² and 10⁶ g/mol. The constituent (A) may be, for example, a relatively low molecular weight oligosiloxane having alkenyl functional groups, such as 1,2-divinyltetramethyldisiloxane, but may also be a highly polymeric polydimethylsiloxane having Si-bonded vinyl groups in the chain or as terminal groups and, for example, having a molecular weight of 10⁵ g/mol (number average determined by means of NMR). The structure of the molecules forming the constituent (A) has also not been established; in particular, the structure of a relatively high molecular weight, i.e. oligomeric or polymeric, siloxane may be linear, cyclic, branched, resin-like, or network-like. Linear and cyclic polysiloxanes are preferably composed of units of the formula R₃SiO₁/₂, R¹R₂SiO₂/₂, R¹RSiO₂/₂ and R₂SiO₂/₂, in which R and R¹ have the abovementioned meaning. Branched and network-like polysiloxanes additionally contain trifunctional and/or tetrafunctional units, those of the formulae RSiO₃/₂, R¹SiO₃/₂ and SiO₄/₂ being preferred. Of course, mixtures of different siloxanes fulfilling the criteria of the constituent (A) may also be used.

Essentially linear polydiorganosiloxanes having vinyl functional groups and a viscosity of from 0.01 to 500,000 Pa·s, more preferably from 0.1 to 100,000 Pa·s, in each case at 25° C., are preferred as component (A).

All organosilicon compounds which have silicon bonded hydrogen functional (Si-H) groups can be used as organosilicon compound (B).

Linear, cyclic or branched organopolysiloxanes comprising units of the formula

(II)

in which

R may be identical or different and has the abovementioned meaning, c is 0, 1, 2 or 3 and d is 0, 1 or 2, with the proviso that the sum of c+d is less than or equal to 3 and on average at least two Si-bonded hydrogen atoms are present per molecule, are preferably used as organopolysiloxanes (B) which have Si-bonded hydrogen atoms. Preferably, the organopolysiloxane (B) used according to the invention contains Si-bonded hydrogen in the range from 0.04 to 1.7% by weight, based on the total weight of the organopolysiloxane (B).

The molecular weight of constituent (B) can likewise vary within wide limits, for example between $10^2$ and $10^6$ g/mol. Thus, constituent (B) may be, for example, a relatively low molecular weight oligosiloxane having SiH functional groups, such as tetramethyldisiloxane, but may also be a highly polymeric polydimethylsiloxane having SiH groups in the chain, or having terminal SiH groups, or may be a silicone resin having SiH groups. The structure of the molecules forming the constituent (B) is also not fixed; in particular, the structure of a relatively high molecular weight, i.e. oligomeric or polymeric SiH-containing siloxane may be linear, cyclic, branched, resin-like, or network-like. Linear and cyclic polysiloxanes are preferably composed of units of the formula $R_3SiO_{1/2}$, $HR_2SiO_{1/2}$, $HRSiO_{2/2}$ and $R_2SiO_{2/2}$, in which R has the abovementioned meaning. Branched and network-like polysiloxanes additionally contain trifunctional and/or tetrafunctional units, those of the formulae $RSiO_{3/2}$, $HSiO_{3/2}$ and $SiO_{4/2}$ being preferred. Of course, mixtures of different siloxanes fulfilling the criteria of constituent (B) may also be used. In particular, the molecules forming the constituent (B) may optionally simultaneously also contain aliphatically unsaturated groups in addition to the obligatory SiH groups. The use of low molecular weight compounds having SiH functional groups, such as tetrakis(dimethylsiloxy)silane and tetramethylcyclotetrasiloxane, and relatively high molecular weight SiH-containing siloxanes, such as poly(hydrogenmethyl)siloxane and poly(dimethylhydrogenmethyl)siloxane, having a viscosity at 25° C. of 10 to 10,000 mPa·s, or analogous SiH-containing compounds in which some of the methyl groups have been replaced by 3,3,3-trifluoropropyl or phenyl groups are particularly preferred.

Constituent (B) is preferably contained in the total crosslinkable silicone materials according to the invention in an amount such that the molar ratio of SiH groups to aliphatically unsaturated groups is from 0.1 to 20, particularly preferably between 1.0 and 5.0.

The components (A) and (B) used according to the invention are commercial products or can be prepared by processes customary in chemistry.

Instead of or in addition to components (A) and (B), the materials according to the invention may contain organopolysiloxanes (C) which have aliphatic carbon-carbon multiple bonds and Si-bonded hydrogen atoms. The use of such multi-functional compounds, however, is not preferred. If siloxanes (C) are used, they are preferably those comprising units of the formulae

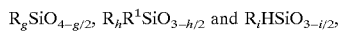

$$R_gSiO_{4-g/2}, R_hR^1SiO_{3-h/2} \text{ and } R_iHSiO_{3-i/2},$$

in which R and $R^1$ have the meanings stated above therefor, and g is 0, 1, 2 or 3, h is 0, 1 or 2 and i is 0, 1 or 2, with the proviso that at least 2 radicals $R^1$ and at least two Si-bonded hydrogen atoms are present per molecule.

Examples of organopolysiloxanes (C) are those comprising $SiO_{4/2}$, $R_3SiO_{1/2}$, $R_2R^1SiO_{1/2}$ and $R_2HSiO_{1/2}$ units, so-called MQ resins, it being possible for these resins additionally to contain $RSiO_{3/2}$ and $R_2SiO$ units, and linear organopolysiloxanes essentially consisting of $R_2R^1SiO_{1/2}$, $R_2SiO$ and RHSiO units, in which R and $R^1$ have the abovementioned meaning. The organopolysiloxanes (C) preferably have an average viscosity of from 0.01 to 500,000 Pa·s, particularly preferably 0.1 to 100,000 Pa·s, in each case at 25° C. Organopolysiloxanes (C) can be prepared by methods customary in chemistry.

Examples of $R^2$ are dienes, such as 1,3-butadiene, 1,4-diphenyl-1,3-butadiene, 1,3-cyclohexadiene, 1,4-cyclohexadiene, 2,4-hexadiene, 1,4-hexadiene, 1,5-hexadiene, 2,5-dimethyl-2,4-hexadiene, α- and γ-terpinene, (R)-(+)-4-isopropenyl-1-methyl-1-cyclohexene, (S)-(-)-4-isopropenyl-1-methyl-1-cyclohexene, 4-vinyl-1-cyclohexene, 2,5-heptadiene, 1,5-cyclooctadiene, 1-chloro-1,5-cyclooctadiene, 1,5-dimethyl-1,5-cyclooctadiene, 1,6-dimethyl-1,5-cyclooctadiene, 1,5-dichloro-1,5-cyclooctadiene, 5,8-dihydro-1,4-dioxocine, $\eta^4$-1,3,5,7-cyclooctatetraene, $\eta^4$-1,3,5-cycloheptatriene, $\eta^4$-1-fluoro-1,3,5,7-cyclooctatetraene, $\eta^4$-1,2,4,7-tetramethyl-1,3,5,7-cyclooctatetraene, 1,8-cyclotetradecadiene, 1,9-cyclohexadecadiene, 1,13-cyclotetracosadiene, $\eta^4$-1,5,9-cyclododecatriene, $\eta^4$-1,5,10-trimethyl-1,5,9-cyclododecatriene, $\eta^4$-1,5,9,13-cyclohexadecatetraene, bicyclo[2.2.1]hepta-2,5-diene, 1,3-dodecadiene, methylcyclopentadiene dimer, 4,7-methylene-4,7,8,9-tetrahydroindene, bicyclo[4.2.2]deca-3,9-diene-7,8-dicarboxylic anhydride, alkyl bicyclo[4.2.2]deca-3,9-diene-7,8-dicarboxylate and alkyl bicyclo[4.2.2]deca-3,7,9-triene-7,8-dicarboxylate.

Diene $R^2$ is preferably 1,5-cyclooctadiene, 1,5-dimethyl-1,5-cyclooctadiene, 1,6-dimethyl-1,5-cyclooctadiene, 1-chloro-1,5-cyclooctadiene, 1,5-dichloro-1,5-cyclooctadiene, 1,8-cyclotetradecadiene, 1,9-cyclohexadecadiene, 1,13-cyclotetracosadiene, bicyclo[2.2.1]hepta-2,5-diene, 4-vinyl-1-cyclohexene and $\eta^4$-1,3,5,7-cyclooctatetraene, 1,5-cyclooctadiene, bicyclo[2.2.1]hepta-2,5-diene, with 1,5-dimethyl-1,5-cyclooctadiene and 1,6-dimethyl-1,5-cyclooctadiene being particularly preferred.

Examples of $R^3$ are alkyl radicals such as the methyl, ethyl, n-propyl, isopropyl, 1-n-butyl, 2-n-butyl, isobutyl, tert-butyl, n-pentyl, isopentyl, neopentyl and tert-pentyl radicals; hexyl radicals such as the n-hexyl radical; heptyl radicals such as the n-heptyl radical; octyl radicals such as the n-octyl radical and the isooctyl radicals, for example the 2,2,4-trimethylpentyl radical; nonyl radicals such as the n-nonyl radical; decyl radicals such as the n-decyl radical; cycloalkyl radicals such as the cyclopropyl, cyclopentyl, cyclohexyl, cycloheptyl, and methylcyclohexyl radicals; unsaturated radicals such as the allyl, 5-hexenyl, 7-octenyl, cyclohexenyl and styryl radicals; aryl radicals such as phenyl radicals, o-, m- and p-tolyl radicals, xylyl radicals and ethylphenyl radicals; aralkyl radicals such as the benzyl radical and the α- and β-phenylethyl radicals; and radicals of the formula $—C(R^1)=CR^1_2$. Further examples of $R^3$ are $—OR^6$ radicals such as hydroxy, methoxy, ethoxy, isopropoxy, butoxy and phenoxy radicals. Examples of halogenated radicals $R^3$ are haloalkyl radicals such as the 3,3,3-trifluoro-n-propyl radical, the 2,2,2,2',2',2'-hexafluoroisopropyl radical, and the heptafluoroisopropyl radical; and haloaryl radicals such as the o-, m- and p-chlorophenyl radicals. Examples of silyl radicals $R^3$ are trimethylsilyl, ethyldimethylsilyl, methoxydimethylsilyl, n-propyldimethylsilyl, isopropyldimethylsilyl, n-butyldimethylsilyl, tert-butyldimethylsilyl, octyldimethylsilyl, vinyldimethylsilyl, phenyldimethylsilyl, diphenylmethylsilyl, hydroxypropyldimethylsilyl, methylvinylphenylsilyl and methoxypropylsilyl radicals.

Radical $R^3$ is preferably a hydrogen atom, a hydroxyl radical, a methoxy radical, a hydrocarbon radical having 1 to 8 carbon atoms, a trimethylsilyl, ethyldimethylsilyl, butyldimethylsilyl, or octyldimethylsilyl radical, with a hydrogen atom, the methyl radical and the trimethylsilyl radical being particularly preferred.

$R^4$ is preferably a monovalent hydrocarbon radical having 1 to 24 carbon atoms, such as the examples stated in connection with radical $R^3$, substituted hydrocarbon radicals such as the hydroxypropyl and chloropropyl radical and —$OR^6$ radicals such as hydroxyl, methoxy and ethoxy radicals, with the methyl, ethyl, butyl, octyl, methoxy, ethoxy and hydroxypropyl radicals being particularly preferred.

Examples of $R^6$ are the radicals stated for $R^3$. $R^6$ is preferably hydrogen, an alkyl radical, or an aryl radical, with a hydrogen atom, the methyl radical and the ethyl radical being particularly preferred.

Examples of radical $R^7$ are the radicals stated for radical $R^3$, and the 1-trimethylsilyloxypropyl-3-dimethylsilyl, 1-ethyldimethylsilyloxypropyl-3-dimethylsilyl, 1-methoxydimethylsilyloxypropyl-3-dimethylsilyl and pentamethyldisiloxanyl radicals. $R^7$ are preferably monovalent radicals, for example, a hydrogen atom, or the methyl, methoxy, trimethylsilyl, octyldimethylsilyl, dimethyhnethoxysilyl, 1-trimethylsilyloxypropyl-3-dimethylsilyl or hydroxypropyldimethylsilyl radicals, or a polyvalent radicals such as —$C_2H_4$—, —$Si(Me)_2$—O—$Si(Me)_2O_{1/2}$, —$Si(Me)_2$—$CH_2$—$CH_2$—$CH_2$—O—$Si(Me)_2O_{1/2}$, —$Si(Me)_2$—O—$Si(Me)O_{2/2}$, —$Si(Me)_2$—O—$SiO_{3/2}$, —$Si(Me)_2$—$CH_2$—$CH_2$—$Si(Me)_2O_{1/2}$ and —$Si(Me)_2$—$CH_2$—$CH_2$—$Si(Me)O_{2/2}$, in which Me denotes a methyl radical.

Examples of radicals $R^8$ are an oxygen atom and —$CH_2$—, —$C_2H_4$—, —$C_3H_6$—, —$C_4H_8$—, —$C_6H_{12}$—, —$C_6H_4$—, —$CH_2CH(CH_3)$—$C_6H_4$—$CH(CH_3)CH_2$— and —$(CH_2)_3O$—, with the oxygen atom, and the —$C_2H_4$—, —$C_3H_6$— and —$(CH_2)_3$— diradicals being particularly preferred.

Examples of radicals $R^9$ are a hydrogen atom and the examples stated for radical R and radical $R^1$. $R^9$ are preferably monovalent hydrocarbon radicals with 1 to 12 carbon atoms, the methyl, ethyl, phenyl and vinyl radicals being particularly preferred. In all these descriptions of various replacement groups for $R^1$ through $R^9$, the exemplified radicals are illustrative, and not limiting.

Examples of the units of the formula (VI) are $SiO_{4/2}$, $(Me)_3SiO_{1/2}$, $Vi(Me)_2SiO_{1/2}$, $Ph(Me)_2SiO_{1/2}$, $(Me)_2SiO_{2/2}$, $Ph(Me)SiO_{2/2}$, $Vi(Me)SiO_{2/2}$, $H(Me)SiO_{2/2}$, $MeSiO_{3/2}$, $PhSiO_{3/2}$, $ViSiO_{3/2}$, $(Me)_2(MeO)SiO_{1/2}$ and $OH(Me)_2SiO_{1/2}$, with $(Me)_3SiO_{1/2}$, $Vi(Me)_2SiO_{1/2}$, $(Me)_2SiO_{2/2}$, $Ph(Me)SiO_{2/2}$, $Vi(Me)SiO_{2/2}$ and $Me_2(MeO)SiO_{1/2}$— $MeSiO_{3/2}$ being preferred, and with $(Me)_3SiO_{1/2}$, $Vi(Me)_2SiO_{1/2}$, $(Me)_2SiO_{2/2}$ and $Vi(Me)SiO_{2/2}$ being particularly preferred. In these formulae, Me is a methyl radical, Vi is a vinyl radical and Ph is a phenyl radical.

A limited number of bis(alkynyl)(η-olefm)platinum compounds and processes for their preparation are known from J. Chem. Soc., Dalton Trans. (1986) 1987–92 and Organometallics (1992) 11 2873–2883. The platinum catalysts (D) according to the invention can be prepared by analogous syntheses and purification steps.

The platinum catalyst (D) used according to the invention is preferably a bis(alkynyl))(1,5-cyclooctadienyl)platinum, bis(alkynyl)(bicyclo[2.2.1]hepta-2,5-dienyl)platinum, bis(alkynyl) (1,5-dimethyl-1,5-cyclooctadienyl)platinum or bis(alkynyl)(1,6-dimethyl-1,5-cyclooctadienyl)platinum complex.

The present invention furthermore relates to platinum complexes of the formula (III) and platinum complexes comprising structural units of the formulae (V) and optionally (VI), those in which $R^2$ are cyclic dienes having 6 to 28 carbon atoms being preferred.

The amount of the platinum catalyst (D) used according to the invention depends on the desired crosslinking rate and on the respective use and economics with respect thereto. The materials according to the invention contain platinum catalysts (D) in amounts of preferably, from 0.05 to 500 ppm by weight (=parts by weight per million parts by weight), more preferably from 0.5 to 100 ppm by weight, and in particular from 1 to 50 ppm by weight, based in each case on the total weight of the material.

In addition to the components (A) to (D), the curable compositions according to the invention may also contain all further substances which have also been used to date for the preparation of addition-crosslinkable materials.

Examples of reinforcing fillers which may be used as component (E) in the materials according to the invention are pyrogenic or precipitated silicic acids having BET surface areas of at least 50 $m^2/g$ and carbon blacks and active carbons, such as furnace black and acetylene black, pyrogenic and precipitated silicic acids having BET surface areas of at least 50 $m^2/g$ being preferred. These silicic acid fillers may have a hydrophilic character or may be rendered hydrophobic by known methods. When hydrophilic fillers are used, the addition of a water repellant agent is required. The content of actively reinforcing filler (E) in the crosslinkable material according to the invention is in the range from 0 to 70% by weight, preferably 0 to 50% by weight.

The silicone rubber material according to the invention can alternatively contain, as constituent (F), further additives in an amount of up to 70% by weight, preferably from 0.0001 to 40% by weight. These additives may be, for example, inactive fillers, resin-like polyorganosiloxanes which differ from the siloxanes (A), (B) and (C), dispersants, solvents, adhesion promoters, pigments, dyes, plasticizers, organic polymers, heat stabilizers, etc. These include additives such as quartz powder, diatomaceous earth, clays, chalk, lithopone, carbon blacks, graphite, metal oxides, metal carbonates, metal sulfates, metal salts of carboxylic acids, metal dusts, fibers, such as glass fibers, plastics fibers, plastics powder, dyes, pigments, etc.

Furthermore, additives (G) which serve for specifically controlling the processing time, initiation temperature and crosslinking rate of the materials according to the invention may also be present. These inhibitors and stabilizers are very well known in the area of addition-crosslinking materials. Examples of customary inhibitors are acetylenic alcohols, such as 1-ethynyl-2-cyclohexanol, 2-methyl-3-butyn-2-ol, 3,5-dimethyl-1-hexyn-3-ol, and 3-methyl-1-dodecyn-3-ol; polymethylvinylcyclosiloxanes; such as 1,3,5,7-tetravinyltetramethyltetrayclosiloxane; low molecular weight silicone oils having methylvinyl-$SiO_{2/2}$ groups and/or $R_2$-vinyl-$SiO_{1/2}$ terminal groups such as divinyltetramethyldisiloxane and tetravinyldimethyldisiloxane; trialkyl cyanurates; alkyl maleates; such as diallyl maleate, dimethyl maleate and diethyl maleate; alkyl fumarates such as diallyl fumarate and diethyl fumarate; organic hydroperoxides such as cumyl hydroperoxide, tert-butyl hydroperoxide and pinane hydroperoxides; organic peroxides; organic sulfoxides; organic amines, diamines and amides; phosphines and phosphites; nitriles, triazoles, diaziridines and oximes. The effect of these inhibitor additives (G) depends on their chemical structure, so that their concentrations in the compositions must be determined individually.

The inhibitor content of the materials according to the invention is preferably from 0 to 50,000 ppm, particularly preferably from 20 to 2000 ppm, in particular from 100 to 1000 ppm.

The organopolysiloxane materials according to the invention can, if required, be dissolved, dispersed, suspended or emulsified in liquids. The materials according to the invention may in particular depending on the viscosity of the constituents and filler content, have a low viscosity and be pourable, may have a pasty consistency, may be pulverulent or may be pliable, highly viscous materials, such physical embodiments being ordinarily the case with the materials denoted by those skilled in the art as RTV-1, RTV-2, LSR and HTV. If the compositions are highly viscous, the materials according to the invention can be prepared in the form of granules. Here, the individual granular particle may contain all components, or the components D and B may be incorporated separately into different granular particles. Regarding the elastomeric properties of the crosslinked silicone materials according to the invention, the entire spectrum is likewise included, beginning with extremely soft silicone gels, through rubber-like materials, to highly crosslinked silicones exhibiting glassy behavior.

The preparation of the organopolysiloxane materials according to the invention can be carried out by known processes, such as, for example, by uniform mixing of the individual components. Any desired sequence may be employed, but the uniform mixing of the platinum catalyst (D) with a mixture of (A), (B), optionally (E), (F) and (G) is preferable. The platinum catalyst (D) used according to the invention can be incorporated as a solid substance or as a solution, dissolved in a suitable solvent, or as a so-called master-batch, in which the catalyst (D) is uniformly mixed with a small amount of (A) or (A) with (E). The mixing is effected as a function of the viscosity of (A), for example by means of a stirrer, in a dissolver, on a roll or in a kneader. The catalyst (D) can also be encapsulated in an organic thermoplastic or thermoplastic silicone resin.

The components (A) to (G) used according to the invention may each be an individual component, or a mixture of at least two different types of such component.

The materials according to the invention which can be crosslinked by addition of an Si-bonded hydrogen at an aliphatic multiple bond can be allowed to crosslink under conventional conditions. Temperatures of from 100° C. to 220° C., more preferably from 130° C. to 190° C., and a pressure of from 900 hPa to 1100 hPa are preferably used here. However, higher or lower temperatures and pressures may also be used. The crosslinking can also be carried out photochemically by means of high-energy radiation, such as, for example, visible light having short wavelengths and UV light, or by a combination of thermal and photochemical excitation.

The present invention furthermore relates to moldings prepared by crosslinking the materials according to the invention.

The materials according to the invention and the crosslinked products produced therefrom according to the invention can be used for all purposes for which organopolysiloxane materials crosslinkable to elastomers or elastomers have previously been used. This includes, for example, silicone coating or impregnation of any desired substrates, the production of shaped articles, for example by the injection molding method, vacuum extrusion method, extrusion method, molding and compression molding, casting, and use as sealing, embedding and casting materials, etc.

The crosslinkable materials according to the invention have the advantage that they can be prepared in a simple process using readily obtainable starting materials and hence may be economically prepared. The crosslinkable materials according to the invention have the further advantage that, as a one-component formulation, they have a good shelf life at 25° C. and ambient pressure, and crosslink rapidly only at elevated temperature. The silicone materials according to the invention have the still further advantage that, in the case of two-component formulation, after mixing of the two components, they give a crosslinkable silicone material whose processibility is retained over a long period at 25° C. and ambient pressure (extremely long pot life) and which crosslinks rapidly only at elevated temperature.

In the preparation of the crosslinkable materials according to the invention, it is a major advantage that the platinum catalyst (D) can be readily incorporated and no solvent is required for this purpose. The materials according to the invention furthermore have the advantage that the crosslinked silicone rubbers have excellent transparency. The materials according to the invention also have the advantage that the hydrosilylation reaction does not slow down with the duration of the reaction, nor even after long storage at room temperature.

The platinum complexes according to the invention are useful as catalysts for the well-known hydrosilylation reaction in organosilicon chemistry, as a catalyst for the hydrogenation of unsaturated organic compounds or polymers, and for the oligomerization of acetylene and other alkynes. The platinum catalysts according to the invention furthermore have the advantage that terminal double bonds do not undergo rearrangement to become internal double bonds in the hydrosilylation reaction, with the result that weakly reactive isomerized starting material would remain. The platinum catalysts according to the invention have the further advantage that no platinum colloids are formed and no discolorations result through their use.

In the examples described below, all data on parts and percentages are based on weight, unless stated otherwise. Unless stated otherwise, the following examples are carried out at a pressure of the ambient atmosphere, i.e. at about 1000 hPa, and at room temperature, i.e. at about 20° C., or at a temperature which is established on combining the reactants at room temperature without additional heating or cooling.

Below, all viscosity data are based on a temperature of 25° C.

COD denotes cycloocta-1,5-diene, $ME_2COD$ denotes a mixture of 1,5-dimethylcycloocta-1,5-diene and 1,6-dimethylcycloocta-1,5-diene, p- denotes para substitution on an aromatic ring, m- denotes meta substitution on an aromatic ring, Vi denotes a vinyl radical, Me denotes a methyl radical and Ph denotes a phenyl radical.

Preparation of Catalyst 1

A suspension of 0.50 g of [$PtCl_2$(COD)] in 20 ml of methanol was cooled to −20° C. under nitrogen. A freshly prepared solution of 0.77 g of (4-trimethylsilylphenylethynyl)trimethylsilane (prepared according to J. Chem. Soc. (C) 1967, 1364–1366) and sodium methanolate (prepared from 61.5 mg of sodium and 15 ml of methanol) was then slowly added dropwise. After about 20 minutes, the mixture was heated to room temperature, and the precipitate was filtered off and was washed five times with acetone. 0.78 g of a platinum complex of the following formula was obtained:

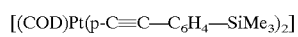

Under analogous conditions, catalyst 1 can also be prepared using 4-trimethylsilylphenylacetylene instead of (4-trimethylsilylphenylethynyl)trimethylsilane.

Preparation of Catalyst 2

A suspension of 0.50 g of [PtCl$_2$(COD)] in 20 ml of methanol was cooled to −20° C. under nitrogen. A freshly prepared solution of 0.77 g of (3-trimethylsilylphenylethynyl)trimethylsilane (prepared according to J. Chem. Soc. (C) 1967, 1364–1366) and sodium methanolate (prepared from 61.5 mg of sodium and 15 ml of methanol) was then slowly added dropwise. After about 20 minutes, the mixture was heated to room temperature, and the precipitate was filtered off and was washed five times with acetone. 0.81 g of a platinum complex of the following formula was obtained:

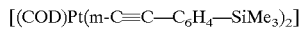
[(COD)Pt(m-C≡C—C$_6$H$_4$—SiMe$_3$)$_2$]

Preparation of Catalyst 3

A suspension of 0.50 g of [PtCl$_2$(COD)] in 15 ml of methanol was cooled to −20° C. under nitrogen. A freshly prepared solution of 0.84 g of (4-dimethyloctylsilylphenylacetylene (preparation analogous to J. Chem. Soc. (C) 1967, 1364–1366, n-octyldimethylchlorosilane being used instead of trimethylchlorosilane) and sodium methanolate (prepared from 61.5 mg of sodium and 15 ml of methanol) was then slowly added dropwise. After about 60 minutes, the mixture was heated to room temperature, and the precipitate was filtered off and was washed five times with acetone. 0.84 g of a platinum complex of the following formula was obtained:

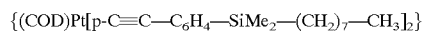
{(COD)Pt[p-C≡C—C$_6$H$_4$—SiMe$_2$—(CH$_2$)$_7$—CH$_3$]$_2$}

Preparation of Catalyst 4

The procedure described above for the preparation of catalyst 1 is repeated with the modification that 0.54 g of [PtCl$_2$(Me$_2$COD)] was used instead of 0.50 g of [PtCl$_2$(COD)]. 0.73 g of the platinum complex of the following formula was obtained:

[(Me$_2$COD)Pt(p-C≡C—C$_6$H$_4$—SiMe$_3$)$_2$]

Preparation of Catalyst 5

A suspension of 0.50 g of [PtCl$_2$(COD)] in 20 ml of methanol was cooled to −20° C. under nitrogen. A freshly prepared solution of 0.72 g of (4-dimethylsilylphenylethynyl)trimethylsilane (prepared analogously to J. Chem. Soc. (C) 1967, 1364–1366, dimethylchlorosilane (commercially available from ABCR GmbH & Co. KG used in lieu of chlorotrimethylsilane) and sodium methanolate (prepared from 61.5 mg of sodium and 15 ml of methanol) was then slowly added dropwise. After about 60 minutes, the mixture was heated to room temperature, and the precipitate was filtered off, stirred in acetone, again filtered and dried in vacuo. 0.83 g of a platinum complex of the following formula was obtained:

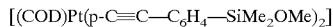
[(COD)Pt(p-C≡C—C$_6$H$_4$—SiMe$_2$OMe)$_2$]

Preparation of Catalyst 6

A suspension of 0.50 g of [PtCl$_2$(COD)] in 20 ml of methanol was cooled to −20° C. under nitrogen. A freshly prepared solution of 1.2 g of (4-trimethylsilyloxypropylphenylethynyl)trimethylsilane (prepared analogously to J. Chem. Soc. (C) 1967, 1364–1366, 3-(trimethylsilyloxypropyl) dimethylchlorosilane (commercially available from ABCR GmbH & Co. KG) being used instead of chlorotrimethylsilane) and sodium methanolate (prepared from 61.5 mg of sodium and 15 ml of methanol) was then slowly added dropwise. After about 20 minutes, the mixture was heated to room temperature, and the precipitate was filtered off, stirred in acetone, filtered off and dried in vacuo. 0.99 g of a platinum complex of the following formula was obtained:

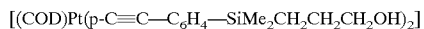
[(COD)Pt(p-C≡C—C$_6$H$_4$—SiMe$_2$CH$_2$CH$_2$CH$_2$OH)$_2$]

Preparation of Catalyst 7

0.5 g of catalyst 6 was suspended in diethyl ether, and 1.13 ml of butyllithium (1.6 M in hexane fraction, obtainable from Sigma-Aldrich Chemie GmbH) was added at 79° C. After thawing at 0° C., 0.15 g of vinyldimethylchlorosilane (obtainable from ABCR GmbH & Co. KG) was added dropwise and stirring was carried out for 1 hour. Thereafter, the mixture was evaporated to dryness, taken up in toluene, filtered off from the LiCl and once again evaporated to dryness. 0.47 g of a platinum complex with the following formula was obtained:

[(COD)Pt(p-C≡C—C$_6$H$_4$—SiMe$_2$CH$_2$CH$_2$CH$_2$OSiMe$_2$Vi)$_2$]

Preparation of Catalyst 8

2.08 g of silanol-terminated polydimethylsiloxane having on average 0.8% by weight of SiOH groups (obtainable from ABCR GmbH & Co. KG), 1.0 g of catalyst 5 and 0.02 g of dibutyl phosphate (obtainable from Sigma-Aldrich Chemie GmbH) were stirred for 2 hours, 0.013 g of titanium(IV) butylate (obtainable from Sigma-Aldrich Chemie GmbH) was then stirred in, and the mixture was filtered. 2.3 g of a platinum complex were obtained, which, according to $^1$H- and $^{29}$Si-NMR, had on average the following formula (any residues of a titanium phosphate compound still present do not present any problems):

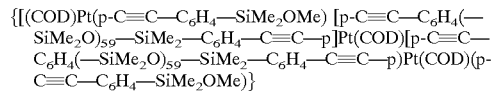
{[(COD)Pt(p-C≡C—C$_6$H$_4$—SiMe$_2$OMe) [p-C≡C—C$_6$H$_4$(—SiMe$_2$O)$_{59}$—SiMe$_2$—C$_6$H$_4$—C≡C—p]Pt(COD)[p-C≡C—C$_6$H$_4$(—SiMe$_2$O)$_{59}$—SiMe$_2$—C$_6$H$_4$—C≡C—p)Pt(COD)(p-C≡C—C$_6$H$_4$—SiMe$_2$OMe)}

EXAMPLE 1

50.0 g of a vinyldimethylsilyloxy-terminated polydimethylsiloxane having a viscosity of 20 Pa·s, 3 mg of 1-ethynyl-1-cyclohexanol and 1.0 g of SiH crosslinking agent were homogeneously mixed with the aid of a stirrer from Janke & Kunkel IKA-Labortechnik, TYPE RE 162, the SiH crosslinking agent being a copolymer comprising dimethylsilyloxy and methyl hydrogensilyloxy and trimethylsilyloxy units, having a viscosity of 330 mPa·s, and a content of Si-bonded hydrogen of 0.46% by weight. 1.7 mg (corresponding to a content of 10 ppm of Pt, based on the total material) of catalyst 1, whose preparation is described above, dissolved in 0.5 ml of methylene chloride, were then stirred in at room temperature.

EXAMPLE 2

The procedure described in Example 1 is repeated, with the modification that 30 mg of ethynylcyclohexanol were stirred in instead of 3 mg of ethynylcyclohexanol.

COMPARATIVE EXAMPLE C1

The procedure described in Example 2 is repeated, with the modification that 10 ppm of platinum as a platinumdivinyltetramethyldisiloxane complex in vinyl-terminated polydimethylsiloxane (commercially available from ABCR GmbH & Co., Germany) were used instead of catalyst 1.

EXAMPLE 3

The procedure described in Example 2 is repeated, with the modification that 1.7 mg of catalyst 2, whose preparation is described above (corresponds to a content of 10 ppm of platinum, based on the total silicone material), were mixed in instead of catalyst 1.

EXAMPLE 4

The procedure described in Example 2 is repeated, with the modification that 2.2 mg of catalyst 3, whose preparation is described above (corresponds to a content of 10 ppm of platinum, based on the total silicone material), were mixed in instead of catalyst 1.

EXAMPLE 5

The procedure described in Example 2 is repeated, with the modification that 1.8 mg of catalyst 4, whose preparation is described above (corresponds to a content of 10 ppm of platinum, based on the total silicone material), were mixed in instead of catalyst 1.

EXAMPLE 6

225 parts by weight of a vinyldimethylsilyloxy-terminated polydimethylsiloxane having a viscosity of 20 Pa·s were initially introduced into a laboratory kneader and heated to 150° C., and 180 parts by weight of a hydrophobic pyrogenic silicic acid having a BET specific surface area of 300 $m^2/g$ and a carbon content of 3.95% by weight were added. A highly viscous material formed and was subsequently diluted with 165 parts by weight of the abovementioned polydimethylsiloxane. By kneading in vacuo (10 mbar) at 150° C. volatile constituents were removed in the course of one hour.

488.1 g of the base material thus prepared were mixed on a roll at a temperature of 25° C. with 0.160 g of inhibitor, 10.95 g of SiH crosslinking agent and 2.0 g of catalyst master-batch to give a homogeneous material, the inhibitor being 1-ethynyl-1-cyclohexanol, the SiH crosslinking agent being a copolymer comprising dimethylsilyloxy and methylhydrogensilyloxy and trimethylsilyloxy units having a viscosity of 320 mPa·s and a content of Si-bonded hydrogen of 0.48% by weight, and the catalyst master-batch being a mixture of the abovementioned vinylpolydimethylsiloxane and catalyst 1, whose preparation is described above (5 ppm platinum content, based on the total material).

COMPARATIVE EXAMPLE C2

The procedure described in Example 6 is repeated, with the modification that 8 ppm of platinum in the form of platinumdivinyltetramethyldisiloxane complex in vinyl-terminated polydimethylsiloxane (commercially available from ABCR GmbH & Co. Germany) were used as catalyst.

EXAMPLE 7

589.4 parts by weight of a vinyldimethylsilyloxy-terminated polydimethylsiloxane having a Brabender plasticity of 630 mkp, corresponding to an average molar mass of about 500,000 g/mol, were mixed with 252.6 parts by weight of a hydrophobic pyrogenic silicic acid having a BET surface area of 300 $m^2/g$ and a carbon content of 3.95% by weight, which was metered in in portions, for 4 hours in a kneader to give a homogeneous material.

500 g of the base material thus obtained were mixed on a roll at a temperature of 20° C. with 0.25 g of inhibitor, 7.5 g of SiH crosslinking agent and 2 g of catalyst master-batch to give a homogeneous material, the inhibitor used being 1-ethynyl-1-cyclohexanol, and the SiH crosslinking agent being a copolymer comprising dimethylsilyloxy and methylhydrogensilyloxy and trimethylsilyloxy units and having a viscosity of 310 mPa·s at 25° C. and a content of Si-bonded hydrogen of 0.46% by weight. The catalyst master-batch is prepared by homogenizing 500 g of the base material described above with 2.1 g of catalyst 1 in a kneader for 30 minutes.

EXAMPLE 8

The procedure described in Example 7 is repeated, with the modification that 5 ppm of platinum as platinum complex 3 were used as catalyst.

EXAMPLE 9

The procedure described in Example 2 is repeated, with the modification that 10 ppm of platinum as platinum complex 5 were used as catalyst.

EXAMPLE 10

The procedure described in Example 2 is repeated, with the modification that 10 ppm of platinum as platinum complex 6 were used as catalyst.

EXAMPLE 11

The procedure described in Example 2 is repeated, with the modification that 10 ppm of platinum as platinum complex 7 were used as catalyst.

EXAMPLE 12

The procedure described in Example 2 is repeated, with the modification that 10 ppm of platinum as platinum complex 8 were used as catalyst.

EXAMPLE 13

The thermal curing properties of the silicone materials prepared in Examples 1, 2, 3, 4, 5, 9, 10, 11 and 12 and Comparative Example 1 (C1) were measured using a Dynamic Analyzer RDA II from Rheometrics, with a heat-up curve from 30 to 200° C. and at a heating rate of 5° C./minute. For the quantitative determination of the storability, the prepared formulation was stored at room temperature (RT) and 50° C., the duration (measured in days) until doubling of the initial value of the viscosity being determined. The results of the measurements are shown in Table 1.

The thermal curing properties of the silicone materials prepared in Examples 6, 7 and 8 and Comparative Example 2 (C2) were measured using a Goettfert Elastograph. For the quantitative determination of the storability, the prepared formulations were stored at room temperature (RT) and 50° C., the duration (measured in days) until doubling of the initial value of the viscosity being determined. The results of the measurements are shown in Table 2.

TABLE 1

| | Example | | | | | | | | | |
|---|---|---|---|---|---|---|---|---|---|---|
| | 1 | 2 | 3 | C1 | 4 | 5 | 9 | 10 | 11 | 12 |
| Initiation temp. [° C.] | 120 | 127 | 112 | 96 | 118 | 108 | 121 | 124 | 119 | 115 |
| Storage at RT | >80 d | >80 d | >78 d | 12 d | >70 d | >70 d | >79 d | >79 d | >79 d | >79 d |
| Storage at 50° C. | 29 d | >80 d | 56 d | 1 d | >70 d | 31 d | 59 d | 54 d | >57 d | 50 d |

The initiation temperature was determined at a heating rate of 5° C./min.
d: days

TABLE 2

| Examples | 6 | C2 | 7 | 8 |
|---|---|---|---|---|
| $a_T$ [° C.] | 126 | 116 | 133 | 127 |
| $t_{90}$ [s] | 26 | 26 | 28 | 28 |
| Storage at RT | >93 d | 15 d | >90 d | >90 d |
| Storage at 50° C. | 63 d | 3 d | 78 d | 45 d | d: days
s: seconds

The initiation temperature $a_T$ was determined at a heating rate of 10° C./min. The temperature which corresponds to the 4% value of the maximum torque was defined as the initiation temperature. The determination of the t₀₀ value was carried out according to DIN 53529 T3. The time from the beginning of the curing to 90% ($t_{90}$ value) of the maximum torque was determined at 180° C.

For further comparison, crosslinked silicone rubber films were produced from some silicone materials immediately after preparation and after storage of the materials for one month at room temperature, and the mechanical properties were determined. Preparation of the crosslinked silicone rubbers was carried out by crosslinking the mixture of the respective example in a hydraulic press at a temperature of 170° C. for 10 minutes to give the silicone rubber. The demolded about 2 mm or 6 mm thick silicone rubber films were subjected to mechanical tests. The result can be seen in Table 3.

TABLE 3

| Immediately after preparation | Hardness [Shore A] | TS [N/mm²] | EB [%] | TPR [N/mm] | R [%] |
|---|---|---|---|---|---|
| Example 6 | 52 | 10 | 590 | 31.5 | 60 |
| Comparison C2 | 51 | 10.6 | 610 | 28.7 | 58 |
| Example 7 | 37 | 12.9 | 1150 | 50.1 | 50 |
| Example 8 | 38 | 12.8 | 1070 | 49.8 | 49 |
| Properties after storage for one month | | | | | |
| Example 6 | 50 | 9.8 | 580 | 30.8 | 62 |
| Comparison C2 | n.a. | n.a. | n.a. | n.a. | n.a. |
| Example 7 | 36 | 12.3 | 1180 | 48.5 | 49 |
| Example 8 | 39 | 13 | 1100 | 48.9 | 47 | n.a. = not applicable, cured after 15 d
Hardness: Shore A hardness was determined according to DIN 53505
TS: Tensile strength was determined according to DIN 53504-S1
EB: Elongation at break was determined according to DIN 53504-S1
TPR: Tear propagation resistance was determined according to ASTM D 624
R: Resilience was determined according to DIN 53512

As is evident from Table 3, the mechanical properties are scarcely changed by storage for one month.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A curable organopolysiloxane composition comprising as curable components (A), (B), and/or (C):

(A) one or more compounds which bear radicals having aliphatic carbon-carbon multiple bonds, (B) one or more organopolysiloxanes having Si-bonded hydrogen atoms, and (C) one or more organopolysiloxanes which have SiC-bonded radicals bearing aliphatic carbon-carbon multiple bonds and Si-bonded hydrogen atoms, wherein said curable component contains at least one of components (A) and (C) having aliphatic carbon-carbon multiple bonds and at least one of components (B) and (C) having Si-bonded hydrogen atoms, and (D) a platinum catalyst comprising at least one platinum catalyst of the formula III

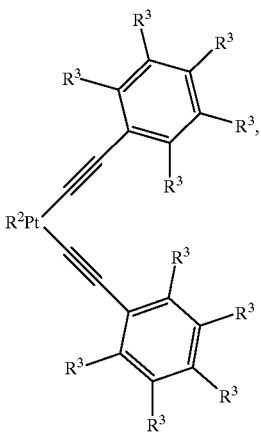

(III)

or an oligomeric or polymeric compound comprising structural units of the general formula

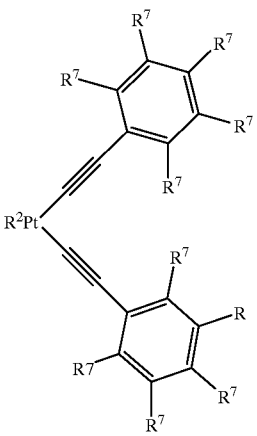

(V)

and optionally structural units of the general formula $$R^9_r SiO_{(4-r)/2} \qquad (VI)$$

in which
- $R^2$ is an optionally substituted diene which is linked by at least one η-bond to platinum and represents a straight or a branched chain having 4 to 18 carbon atoms or a cyclic ring having 6 to 28 carbon atoms,
- $R^3$ is identical or different and is a hydrogen atom, a halogen atom, $—SiR^4_3$, $—OR^6$, or a monovalent, optionally substituted hydrocarbon radical having 1 to 24 carbon atoms, with the proviso that, in the compounds of the formula (III), at least one radical $R^3$ denotes $—SiR^4_3$,
- $R^4$ is identical or different and is hydrogen, a halogen atom, $—OR^6$, or a monovalent, optionally substituted hydrocarbon radicals having 1 to 24 carbon atoms,
- $R^6$ is identical or different and is a hydrogen atom, $—SiR^4_3$, or a monovalent, optionally substituted hydrocarbon radical having 1 to 20 carbon atoms,
- $R^7$ is identical or different and is a hydrogen atom, a halogen atom, $—SiR^4_3$, $—SiR^4_{(3-t)}[R^8 SiR^9_s O_{(3-s)/2}]_t$, $—OR^6$, or a monovalent, optionally substituted hydrocarbon radical having 1 to 24 carbon atoms, with the proviso that, in formula (V), at least one radical $R^7$ denotes $—SiR^4_{(3-t)}[R^8 SiR^9_s O_{(3-s)/2}]_t$,
- $R^8$ is identical or different and is oxygen, or a divalent, optionally substituted hydrocarbon radical having 1 to 24 carbon atoms, which may be bonded to the silicon via an oxygen atom,
- $R^9$ is identical or different and is hydrogen or an organic radical,
- r is 0, 1, 2 or 3,
- s is 0, 1, 2 or 3 and
- t is 1, 2 or 3.

2. The curable organopolysiloxane material of claim 1, wherein constituent (A) is an aliphatically unsaturated organosilicon compound.

3. The curable organopolysiloxane material of claim 2, wherein the organosilicon compound (A) is a linear or branched organopolysiloxane comprising units of the formula $$R_a R^1_b SiO_{(4-a-b)/2} \qquad (I)$$

in which
- R is identical or different and is a monovalent organic radical, free of aliphatic carbon-carbon multiple bonds,
- $R^1$ is identical or different and is a monovalent, optionally substituted SiC-bonded hydrocarbon radical having an aliphatic carbon-carbon multiple bond,
- a is 0, 1, 2 or 3 and
- b is 0, 1 or 2
with the proviso that the sum a+b is less than or equal to 3 and at least 2 radicals $R^1$ are present per molecule.

4. The curable organopolysiloxane material of claim 2, wherein radical R is a monovalent, SiC-bonded hydrocarbon radical free of aliphatic carbon-carbon multiple bonds and having 1 to 6 carbon atoms.

5. The curable organopolysiloxane material of claim 1, wherein at least one of said compounds which bear radicals having aliphatic carbon-carbon multiple bonds (A) comprise a linear or branched organopolysiloxane comprising units of the formula $$R_a R^1_b SiO_{(4-a-b)/2} \qquad (I)$$

in which
- R is identical or different and is a monovalent organic radical, free of aliphatic carbon-carbon multiple bonds,
- $R^1$ is identical or different and is a monovalent, optionally substituted SiC-bonded hydrocarbon radical having an aliphatic carbon-carbon multiple bond,
- a is 0, 1, 2 or 3 and
- b is 0, 1 or 2
with the proviso that the sum a+b is less than or equal to 3 and at least 2 radicals $R^1$ are present per molecule.

6. The curable organopolysiloxane material of claim 5, wherein radical R is a monovalent, SiC-bonded hydrocarbon radical free of aliphatic carbon-carbon multiple bonds and having 1 to 6 carbon atoms.

7. The curable organopolysiloxane material of claim 5, wherein radical R is a monovalent, SiC-bonded hydrocarbon radical free of aliphatic carbon-carbon multiple bonds and having 1 to 6 carbon atoms.

8. The curable organopolysiloxane material of claim 1, wherein the organopolysiloxane (B) comprises a linear, cyclic or branched organopolysiloxane comprising units of the formula $$R_c H_d SiO_{(4-c-d)/2} \qquad (II)$$

in which
- R is identical or different and is a monovalent organic radical, free of aliphatic carbon-carbon multiple bonds,
- c is 0, 1, 2 or 3 and
- d is 0, 1 or 2,
with the proviso that the sum of c+d is less than or equal to 3 and at least two Si-bonded hydrogen atoms are present per molecule.

9. The curable organopolysiloxane material of claim 2, wherein the organopolysiloxane (B) comprises a linear, cyclic or branched organopolysiloxane comprising units of the formula $$R_c H_d SiO_{(4-c-d)/2} \qquad (II)$$

in which
- R is identical or different and is a monovalent organic radical, free of aliphatic carbon-carbon multiple bonds,
- c is 0, 1, 2 or 3 and
- d is 0, 1 or 2,
with the proviso that the sum of c+d is less than or equal to 3 and at least two Si-bonded hydrogen atoms are present per molecule.

10. The curable organopolysiloxane material of claim 3, wherein the organopolysiloxane (B) comprises a linear, cyclic or branched organopolysiloxane comprising units of the formula $$R_c H_d SiO_{(4-c-d)/2} \qquad (II)$$

in which
R is identical or different and is a monovalent organic radical, free of aliphatic carbon-carbon multiple bonds,
c is 0, 1, 2 or 3 and
d is 0, 1 or 2,
with the proviso that the sum of c+d is less than or equal to 3 and at least two Si-bonded hydrogen atoms are present per molecule.

11. The curable organopolysiloxane material of claim 5, wherein the organopolysiloxane (B) comprises a linear, cyclic or branched organopolysiloxane comprising units of the formula $$R_cH_dSiO_{(4-c-d)/2} \tag{II}$$

in which
R is identical or different and is a monovalent organic radical, free of aliphatic carbon-carbon multiple bonds,
c is 0, 1, 2 or 3 and
d is 0, 1 or 2,
with the proviso that the sum of c+d is less than or equal to 3 and at least two Si-bonded hydrogen atoms are present per molecule.

12. The curable organopolysiloxane material of claim 1, wherein the $R^2Pt$ moiety of catalyst (D) comprises one or more of bis(alkynyl)(1,5-cyclooctadienyl)platinum, bis(alkynyl)(bicyclo[2.2.1]hepta-2,5-dienyl)platinum, bis(alkynyl)(1,5-dimethyl-1,5-cyclooctadienyl)platinum and bis(alkynyl)(1,6-dimethyl-1,5-cyclooctadienyl)platinum.

13. A molding produced by crosslinking the composition of claim 1.

14. A platinum complex of the formula (III):

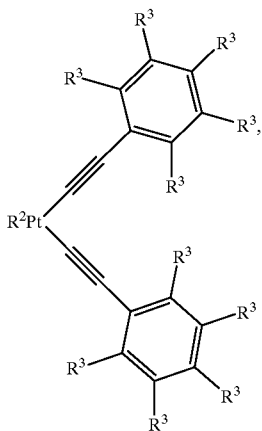

(III)

$R^2$ is an optionally substituted diene which is linked by at least one η-bond to platinum and represents a straight or a branched chain having 4 to 18 carbon atoms or a cyclic ring having 6 to 28 carbon atoms, $R^3$ is identical or different and is a hydrogen atom, a halogen atom, $-SiR^4_3$, $-OR^6$, or a monovalent, optionally substituted hydrocarbon radical having 1 to 24 carbon atoms, with the proviso that, in the compounds of the formula (III), at least one radical $R^3$ denotes $-SiR^4_3$, $R^4$ is identical or different and is hydrogen, a halogen atom, $-OR^6$, or a monovalent, optionally substituted hydrocarbon radicals having 1 to 24 carbon atoms, $R^6$ is identical or different and is a hydrogen atom, $-SiR^4_3$, or a monovalent, optionally substituted hydrocarbon radical having 1 to 20 carbon atoms.

15. The platinum complex as claimed in claim 14, wherein $R^2$ denotes a cyclic diene having 6 to 28 carbon atoms.

16. A platinum complex comprising structural units of the formulae (V)

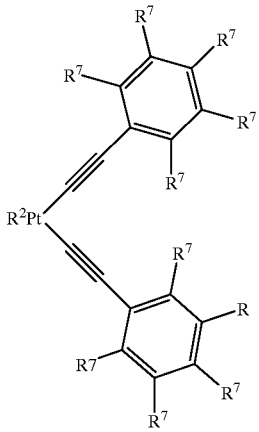

(V)

$R^2$ is an optionally substituted diene which is linked by at least one η-bond to platinum and represents a straight or a branched chain having 4 to 18 carbon atoms or a cyclic ring having 6 to 28 carbon atoms, $R^4$ is identical or different and is hydrogen, a halogen atom, $-OR^6$, or a monovalent, optionally substituted hydrocarbon radicals having 1 to 24 carbon atoms, $R^6$ is identical or different and is a hydrogen atom, $-SiR^4_3$, or a monovalent, optionally substituted hydrocarbon radical having 1 to 20 carbon atoms, $R^7$ is identical or different and is a hydrogen atom, a halogen atom, $-SiR^4_3$, $-SiR^4_{(3-t)}[R^8SiR^9_sO_{(3-s)/2}]_t$, $-OR^6$, or a monovalent, optionally substituted hydrocarbon radical having 1 to 24 carbon atoms, with the proviso that, in formula (V), at least one radical $R^7$ denotes $-SiR^4_{(3-t)}[R^8SiR^9_sO_{(3-s)/2}]_t$, $R^8$ is identical or different and is oxygen, or a divalent, optionally substituted hydrocarbon radical having 1 to 24 carbon atoms, which may be bonded to the silicon via an oxygen atom, $R^9$ is identical or different and is hydrogen or an organic radical, is 0, 1, 2 or 3, s is 0, 1, 2 or 3 and is 1, 2 or 3;

and optionally (VI)

$$R^9_rSiO_{(4-r)/2} \tag{VI}$$

$R^9$ is identical or different and is hydrogen or an organic radical.

17. The platinum complex as claimed in claim 16, wherein $R^2$ denotes a cyclic diene having 6 to 28 carbon atoms.

* * * * *